(12) United States Patent
Liebens et al.

(10) Patent No.: US 8,558,020 B2
(45) Date of Patent: Oct. 15, 2013

(54) AQUEOUS HYDROGEN PEROXIDE SOLUTION, PROCESS FOR ITS PREPARATION AND USE THEREOF

(75) Inventors: Armin T. Liebens, Braine l'Alleud (BE); Jean-Pierre Ganhy, Brussels (BE); Jean-Pierre Catinat, Waudrez (BE); Koen Vermeiren, Halle (BE)

(73) Assignee: Solvay (Societe Anonyme), Brussels (BE)

( * ) Notice: Subject to any disclaimer, the term of this patent is extended or adjusted under 35 U.S.C. 154(b) by 3 days.

(21) Appl. No.: 12/593,958

(22) PCT Filed: Mar. 20, 2008

(86) PCT No.: PCT/EP2008/053423
§ 371 (c)(1),
(2), (4) Date: Sep. 30, 2009

(87) PCT Pub. No.: WO2008/122503
PCT Pub. Date: Oct. 16, 2008

(65) Prior Publication Data
US 2010/0113808 A1    May 6, 2010

(30) Foreign Application Priority Data
Apr. 5, 2007    (EP) .................................... 07105712

(51) Int. Cl.
*C07D 303/00*    (2006.01)
*C01B 31/00*    (2006.01)

(52) U.S. Cl.
USPC ........ 549/512; 423/659; 423/584; 423/415.1; 549/200; 549/513; 549/514; 549/523; 549/518

(58) Field of Classification Search
USPC ....................... 423/415.1, 659, 584
See application file for complete search history.

(56) References Cited

U.S. PATENT DOCUMENTS 2,017,440 A * 10/1935 Hawkinson .................... 423/584
4,320,102 A    3/1982 Dalton et al.
4,483,997 A * 11/1984 McEntire et al. ............. 549/529
5,906,738 A *  5/1999 Morisaki et al. ........... 210/257.2

(Continued)

FOREIGN PATENT DOCUMENTS

DE    19936547 A1    2/2001
EP    0965562 A1    12/1999

(Continued)

OTHER PUBLICATIONS

Unknown Author, CEFIC Peroxygens H2O2 standard AM-7160, Mar. 2003—'Hydrogen peroxide for industrial use. Determination of apparent pH (pHa)—Potentiometric method'—7 pp.

(Continued)

*Primary Examiner* — Melvin C Mayes
*Assistant Examiner* — Melissa Stalder
(74) *Attorney, Agent, or Firm* — Brinks Hofer Gilson & Lione

(57) ABSTRACT

The present invention refers to an aqueous hydrogen peroxide solution having a hydrogen peroxide concentration $[H_2O_2]$ expressed as % by weight of the solution and an apparent pH of from $pH_{min}$ to $pH_{max}$, such that $pH_{min}=3.45-0.0377\times[H_2O_2]$, and $pH_{max}=3.76-0.0379\times[H_2O_2]$. The present invention also relates to a process for the preparation of said hydrogen peroxide solution and the use of said solution in a process for the epoxidation of olefins.

28 Claims, 1 Drawing Sheet

(56) References Cited

U.S. PATENT DOCUMENTS

| | | | |
|---|---|---|---|
| 6,224,845 | B1 | 5/2001 | Pennetreau et al. |
| 6,372,924 | B2 | 4/2002 | Thiele |
| 6,380,407 | B1 | 4/2002 | Catinat et al. |
| 6,429,322 | B1 | 8/2002 | Catinat et al. |
| 6,673,950 | B1 | 1/2004 | Teles et al. |
| 6,699,812 | B2 | 3/2004 | Strebelle et al. |
| 6,960,671 | B2 * | 11/2005 | Cooker et al. ............... 549/533 |
| 7,722,847 | B2 * | 5/2010 | Haas et al. .................... 423/272 |
| 2003/0162983 | A1 | 8/2003 | Strebelle et al. |
| 2003/0187285 | A1 | 10/2003 | Balthasart et al. |
| 2004/0068127 | A1 | 4/2004 | Schoebrecht et al. |
| 2004/0167342 | A1 | 8/2004 | Strebelle et al. |
| 2006/0041150 | A1 | 2/2006 | Catinat et al. |
| 2006/0122409 | A1 | 6/2006 | Catinat et al. |
| 2006/0167288 | A1 | 7/2006 | Strebelle et al. |
| 2008/0132718 | A1 | 6/2008 | Strebelle et al. |

FOREIGN PATENT DOCUMENTS

| | | |
|---|---|---|
| EP | 0999181 A1 | 5/2000 |
| EP | 1122249 A1 | 8/2001 |
| FR | 2772740 A1 | 6/1999 |
| FR | 2846965 A1 | 5/2004 |
| GB | 432915 A | 8/1935 |
| GB | 438886 A | 11/1935 |
| GB | 695325 A | 8/1953 |
| WO | WO 99/40024 A1 | 8/1999 |
| WO | WO 99/48882 A1 | 9/1999 |
| WO | WO 99/48883 A1 | 9/1999 |
| WO | WO 02/00634 A | 1/2002 |
| WO | WO 02/00635 A1 | 1/2002 |
| WO | WO 02/092586 A1 | 11/2002 |
| WO | WO 2004/028962 A1 | 4/2004 |
| WO | WO 2007/048808 A1 | 5/2007 |
| WO | WO 2009/027439 A2 | 3/2009 |

OTHER PUBLICATIONS

Unknown Author, CEFIC Peroxygens H2O2 standard AM-7159, Mar. 2003—'Hydrogen peroxide for industrial use. Determination of apparent pH—Titrimetric method' —8 pp.

Elvers et al., Editors, Ullmann's Encyclopedia of Industrial Chemistry—5th Edition, vol. A13, 'High Performance Fibers from Imidazole and Derivatives', p. 447-457, 1989—13 pp.

\* cited by examiner

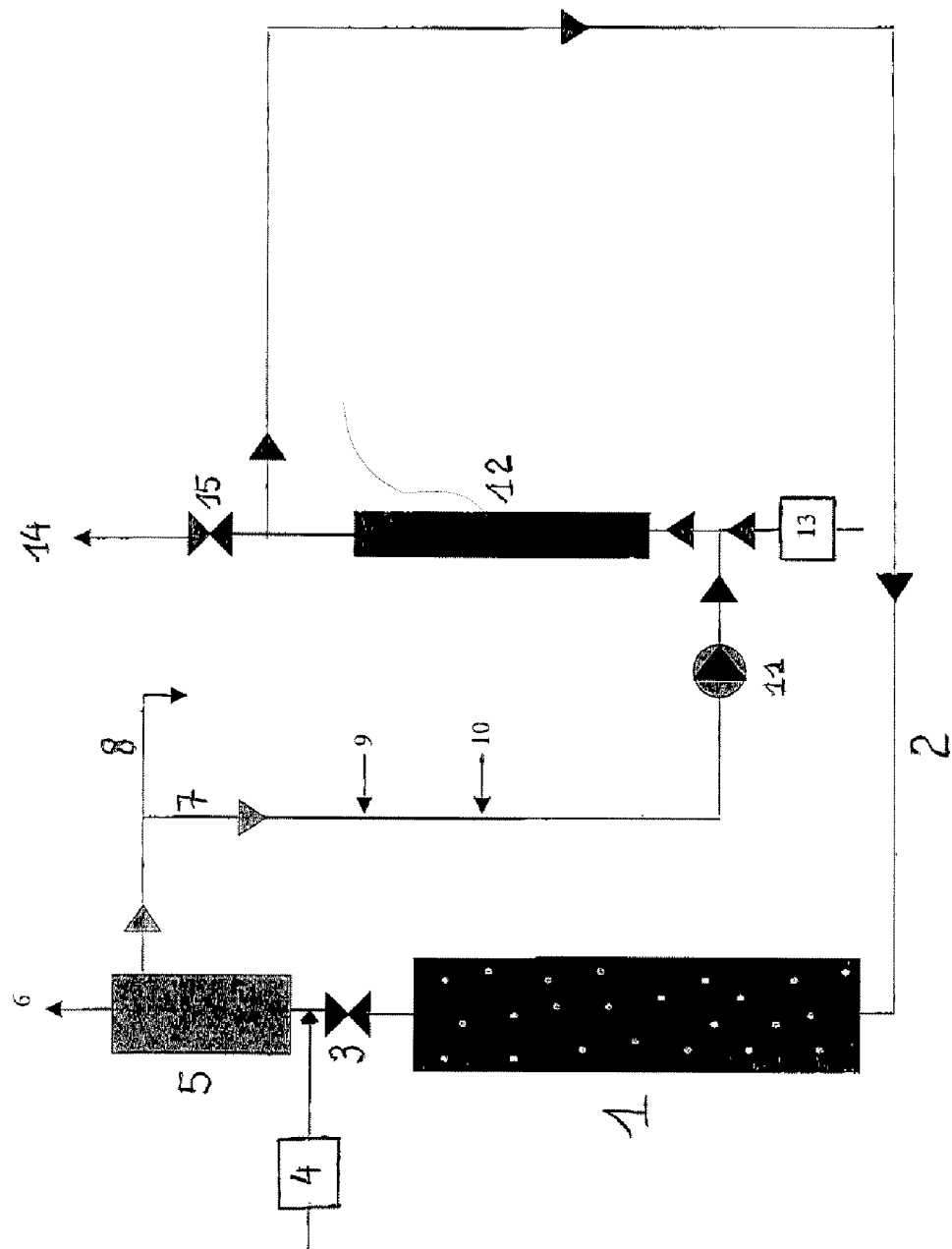

AQUEOUS HYDROGEN PEROXIDE SOLUTION, PROCESS FOR ITS PREPARATION AND USE THEREOF

CROSS-REFERENCE TO RELATED APPLICATIONS

The present application is a U.S. national stage application under 35 U.S.C. §371 of International Application No. PCT/EP2008/053423 filed Mar. 20, 2008, which claims the benefit of the European Patent application filed as EP 07105712.9 on Apr. 5, 2007, the content of each of these applications being incorporated herein by reference for all purposes.

The present application claims the benefit of the European Patent application filed as EP 07105712.9 on Apr. 5, 2007.

BRIEF DESCRIPTION OF THE DRAWING

FIG. 1 is a schematic flow diagram of an experimental set-up used for several example as described in greater detail below.

DETAILED DESCRIPTION

The present invention relates to a specific aqueous hydrogen peroxide solution. In particular, it is related to an aqueous hydrogen peroxide solution having an apparent pH in a specific range. The present invention also refers to an aqueous hydrogen peroxide solution having a specific TOC content. The present invention also relates to a process for the preparation of said hydrogen peroxide solution, as well as to the use of said solution in a process for the epoxidation of olefins. It is known to use hydrogen peroxide in the presence of a heterogeneous catalyst to convert an olefin into an oxirane, more particularly to convert propylene into propylene oxide (1,2-epoxypropane) by reaction with hydrogen peroxide. In this field, many investigations have been done in order to increase the selectivity and/or the activity (conversion rate) of the catalyst. The effect of the addition of basic, acidic and ionic compounds, either during preparation of the catalyst or during the reaction, on the selectivity and activity of the catalyst has notably been studied. As was illustrated in DE 199 36 547, other important parameters are the reaction temperature and the pH of the reaction mixture which can be adjusted in order to keep the conversion rate constant.

The international patent application WO 2004/028962 discloses an aqueous hydrogen peroxide solution characterized by a maximum amount of alkali metals, alkaline earth metals, and amines having a $pK_B$ of less than 4.5 that is particularly suitable for the epoxidation of olefins in the presence of a heterogeneous catalyst. According to this international patent application, there is still a need for new hydrogen peroxide solutions and/or reaction parameters in order to improve the long term activity and selectivity of the catalyst.

The purpose of the present invention is to provide a new aqueous hydrogen peroxide solution that can be safely handled, stored, and shipped, that is suitable for the epoxidation of olefin in the presence of a heterogeneous catalyst and that ensures improved selectivity of the catalyst towards oxiranes (such as propylene oxide and epichlorohydrin) without impairing the hydrogen peroxide conversion rate or even while improving it.

The present invention therefore relates to an aqueous hydrogen peroxide solution having a hydrogen peroxide concentration $[H_2O_2]$ expressed as % by weight of the solution and an apparent pH of from $pH_{min}$ to $pH_{max}$, such that $$pH_{min} = 3.45 - 0.0377 \times [H_2O_2]$$

$$pH_{max} = 3.76 - 0.0379 \times [H_2O_2].$$

One of the essential features of the present invention resides in the apparent pH of the hydrogen peroxide solution which must be of from $pH_{min}$ to $pH_{max}$, $pH_{min}$ and $pH_{max}$ being dependant on the hydrogen peroxide concentration $[H_2O_2]$ expressed as % by weight of the solution according to the following formulas:

$$pH_{min} = 3.45 - 0.0377 \times [H_2O_2]$$

$$pH_{max} = 3.76 - 0.0379 \times [H_2O_2].$$

For example, for a hydrogen peroxide concentration $[H_2O_2]$ of 40% by weight, the apparent pH according to the invention should be of from 1.94 to 2.24.

It has indeed surprisingly been found that the apparent pH of the hydrogen peroxide solution has an impact on the selectivity when this solution is used for the epoxidation of olefins (such as propylene or allyl chloride) into oxiranes (such as propylene oxide or epichlorohydrin). It has further been found that the apparent pH of the solution depends on the hydrogen peroxide concentration $[H_2O_2]$ expressed as % by weight of the solution. The use of a hydrogen peroxide solution having a pH lower than the optimal pH range leads to a lower selectivity. The use of a hydrogen peroxide solution having a pH higher than the optimal pH range leads to a lower selectivity and a lower conversion rate of the hydrogen peroxide. The use of a hydrogen peroxide solution having an optimal pH according to the present invention therefore leads to an optimal selectivity. In addition, the fact of using a hydrogen peroxide solution having such an optimal apparent pH does not impair the hydrogen peroxide conversion rate and can even improve it.

The expression "apparent pH" is the pH measured according to a method based on the CEFIC PEROXYGENS $H_2O_2$ AM-7160 standard (March 2003), describing a potentiometric method for the determination of the apparent pH of a hydrogen peroxide solution. The measurement method is described in detail in the examples.

In the process according to the invention, the aqueous hydrogen peroxide solution can be obtained according to any method known to those skilled in the art. Preferably, the hydrogen peroxide solution is obtained according to the well-known alkylanthraquinone(s), or AO processes (see, for example, "Ullmann's Encyclopedia of Industrial Chemistry, Fifth Edition, 1989, Volume 3, pages 447-457"). The expression "alkylanthraquinone process" is intended to denote a process for producing an aqueous hydrogen peroxide solution which consists in subjecting a working solution of at least one alkylanthraquinone and/or of at least one tetrahydroalkylanthraquinone to a hydrogenation step, in a diluent, to produce one or more alkylanthrahydroquinones and/or alkyltetrahydroanthraquinones. The working solution leaving the hydrogenation step is then subjected to an oxidation with oxygen, air or oxygen-enriched air to give hydrogen peroxide and to reform the alkylanthraquinones and/or alkyltetrahydroanthraquinones. The hydrogen peroxide formed is then separated from the working solution by means of an extraction step, for example using water, the hydrogen peroxide being recovered in the form of a crude aqueous hydrogen peroxide solution. The working solution leaving the extraction step is then recycled into the hydrogenation step in order to recommence the hydrogen peroxide production cycle.

The term "alkylanthraquinones" is intended to denote, for example, 9,10-anthraquinones substituted in position 1, 2 or 3 with at least one alkyl side chain of linear or branched aliphatic type comprising at least one carbon atom. These alkyl chains usually comprise less than 9 carbon atoms and preferably less than 6 carbon atoms. Examples of such alkylanthraquinones are 2-ethylanthraquinone, 2-isopropylanthraquinone, 2-sec- and 2-tert-butylanthraquinone, 1,3-, 2,3-, 1,4- and 2,7-dimethylanthraquinone, and 2-iso- and 2-tert-amylanthraquinone, and mixtures of theses quinones.

The term "alkyanthrahydroquinones" is intended to denote the 9,10-hydroquinones corresponding to the 9,10-alkyanthraquinones specified above.

The crude aqueous hydrogen peroxide solution obtained further to the alkylanthraquinone process can be used in the epoxidation reaction without undergoing any subsequent washing and/or purification treatment.

In another embodiment, which is preferred, the crude aqueous hydrogen peroxide solution obtained from the alkylanthraquinone process can be further subjected to at least one subsequent purification step. The subsequent purification step can consist of any method which is well known to those skilled in the art for reducing the impurity content of an aqueous hydrogen peroxide solution. A distillation step is for example suitable for use. Another type of purification step which can be employed is a washing operation with at least one organic solvent, as the one described in European patent application EP 0965562. This document is incorporated herein by reference.

The crude aqueous hydrogen peroxide solution obtained further to the alkylanthraquinone process can be used in the epoxidation reaction without any additional purification step, therefore avoiding cost- and labor-intensive purification steps.

The aqueous hydrogen peroxide solution according to the invention generally has a hydrogen peroxide concentration $[H_2O_2]$ expressed as % by weight of the solution of less than 80%, preferably of less than 75%, more preferably of less than 60%. The hydrogen peroxide concentration $[H_2O_2]$ is in general more than 5%, in particular more than 10%, in many cases more than 20%, or even more than 30%. Concentrations of at least 32%, at least 35%, at least 38%, are usual. For example, hydrogen peroxide concentrations of around 40% or 50% are common.

The apparent pH of the aqueous hydrogen peroxide solution according to the invention may be adjusted to the sought value by the addition of a strong mineral acid, preferably of nitric acid and/or phosphoric acid.

The apparent pH of the aqueous hydrogen peroxide solution according to the invention is in many cases lower than 2.60; often lower than or equal to 2.55; commonly lower than or equal to 2.50; for instance lower than or equal to 2.45.

The apparent acidity (or apparent pH) of hydrogen peroxide solutions is determined according to the CEFIC PEROXYGENS $H_2O_2$ AM-7159 standard (March 2003), describing the titration of a diluted sample of hydrogen peroxide (max. 4.5% w/w) with a sodium hydroxide solution, using an indicator or a pH electrode. The acid concentration of the aqueous hydrogen peroxide solutions according to the invention is determined after dissolution of 10 ml of the hydrogen peroxide sample with 200 ml of water and by using sodium hydroxide solution having a concentration of 0.01 mol/l and a combined glass pH electrode, the titration being conducted to pH 5.3. The apparent acidity is expressed in millimol of sodium hydroxide/l. The aqueous hydrogen peroxide solution according to the invention usually has an apparent acid concentration measured by titration of from 0.1 to 5 mmol/l, preferably of from 0.15 to 2.5 mmol/l, more preferably of from 0.25 to 1.5 mmol/l, especially of from 0.3 to 0.8 mmol/l. The apparent acidity can also be expressed calculated in equivalents of mg/l $HNO_3$. The aqueous hydrogen peroxide solution according to the invention usually has an apparent acid concentration measured by titration of from 5 to 300 mg/l $HNO_3$, preferably of from 10 to 150 mg/l $HNO_3$, more preferably of from 15 to 100 mg/l $HNO_3$, especially of from 20 to 50 mg/l $HNO_3$.

The aqueous hydrogen peroxide solution of the invention also usually contains organic impurities (products of degradation of the quinone shuttle, traces of diluent) and inorganic impurities (cations and anions introduced by the extraction water, as well as those already present in the mixture derived from the oxidation of the alkylanthraquinone(s)).

The aqueous hydrogen peroxide solution may thus comprise organic impurities expressed as TOC (total organic carbon concentration), defined according to ISO standard 8245. Such TOC is in general at least 0.01 ppm, preferably at least 10 ppm, in particular at least 50 ppm, values of at least 100 ppm giving good results. The TOC is usually at most 500 ppm, in many cases at most 300 ppm, values of at most 250 ppm being common. Suitable ranges for the TOC content are from 0.01 to 500 ppm, preferably from 50 to 300 ppm, especially from 100 to 250 ppm.

The TOC usually contains organic compounds such as, for example, dimethyheptanol (DMH), diisobutylcarbinol (DiBC), 2,6-dimethyl-1,4-heptanediol ($C_9H_{20}O_2$), methyl cyclohexyl acetate, methyl cyclo hexanol, tetrabutyl urea (TBU), trioctyophosphate (TOP), and/or degradation products of alkylated aromatic solvents such as Solvesso 150, i.e. corresponding to the product compounds oxidized on their alkyl chain.

In a preferred embodiment, the TOC contains at least diisobutycarbinol (DiBC), methyl cyclohexyl acetate, tetrabutyl urea (TBU), and/or trioctyophosphate (TOP) as organic compound. For example, the hydrogen peroxide solution according to the invention may be doped with DiBC, methyl cyclohexyl acetate, TBU and/or TOP in an amount of from 30 to 200 ppm by weight of solution, preferably of from 50 to 150 ppm, an amount of about 100 ppm being common.

As explained above, the aqueous hydrogen peroxide solution may also contain metal cations such as alkali metals or alkaline earth metals, for instance sodium, and/or anions such as phosphates, nitrates, etc. in low contents. The alkaline and alkaline earth metals are usually present in an amount of from 1 to 200 ppm, preferably of from 20 to 30 ppm, based on the weight of the solution. The anions are generally present in an amount of from 50 to 500 ppm, of preferably of from 100 to 300 ppm based on the weight of the solution.

An example of an aqueous hydrogen peroxide solution according to the invention is an aqueous hydrogen peroxide solution having a hydrogen peroxide concentration $[H_2O_2]$ of from 38 to 42% by weight, an apparent pH comprised in the range of from $pH_{min}$ to $pH_{max}$ defined according to the invention, namely respectively of from 2.02 to 1.87 and of from 2.31 to 2.17, a TOC content of from 150 to 220 ppm, a content of alkaline and alkaline earth metals of from 20 to 30 ppm, and an anion content of from 100 to 300 ppm.

The aqueous hydrogen peroxide solution of the invention may also contain additives, amongst which stabilizers. Such stabilizers may be chosen from nitric acid, phosphoric acid, benzoic acid, dipicolinic acid (DPA), from salts chosen from nitrate, phosphate, pyrophosphate, stannate, benzoate, salicylate, diethylene triamine penta (methylene phosphonate), and mixtures thereof. The salts may be ammonium or alkaline metal salts, especially ammonium or sodium salts. The stabilizer is preferably chosen from nitric acid, phosphoric acid, di-sodium pyrophosphate, ammonium nitrate, sodium nitrate, sodium stannate, and mixtures thereof. The stabilizer is more preferably chosen from nitric acid, phosphoric acid, di-sodium pyrophosphate, and mixtures thereof. The stabilizer is usually added in amount of from 10 to 200 ppm, preferably of from 50 to 150 ppm, values of 100 ppm being common. Those amounts are those based on the weight of the solution.

The present invention also relates to a process for the preparation of the aqueous hydrogen peroxide solution of the invention according to the anthraquinone loop process. The process according to the invention comprises the following steps:
a) hydrogenation of a working solution comprising at least one organic solvent and at least one anthraquinone compound,
b) oxidation of the hydrogenated working solution to form hydrogen peroxide,
c) extraction of the hydrogen peroxide with an aqueous medium,
d) optionally adding a stabilizer to the extracted aqueous hydrogen peroxide solution,
e) concentrating the aqueous hydrogen peroxide solution to the desired hydrogen peroxide concentration, and
f) optionally, adapting the pH of the aqueous hydrogen peroxide solution.

A survey of the well-known anthraquinone process and its numerous modifications is given in the "Ullmann's Encyclopedia of Industrial Chemistry", Fifth Edition, 1989, Volume 3, pages 447-457. For each of the distinct process steps, the Ullmann reference discloses numerous different possibilities.

The hydrogen peroxide concentration of the solution obtained from the process of the present invention can be adapted, by concentration or dilution operation, before to be used for the epoxidation of olefins.

The pH of the solution obtained from the process of the present invention can be adapted, if necessary, by adding thereto the required amount of acid or base. Typical acids are strong mineral acids such as phosphoric acid and /or nitric acid. A typical base is sodium hydroxide.

The hydrogen peroxide solution of the present invention is particularly suitable for use in a process for the epoxidation of olefins in the presence of a heterogeneous catalyst. Such process for the epoxidation of olefins is preferably conducted in the presence of a water-miscible solvent. Preferably, the solvent is methanol. Preferably, the heterogeneous catalyst is a zeolite based catalyst, more preferably a titanium silicalite based catalyst known as TS-1. The reaction between the olefin and the hydrogen peroxide may be performed in continuous or batchwise mode. It is preferably performed continuously. Advantageously, the oxirane produced is removed from the reaction medium by depressurization and/or by stripping using a gaseous compound. In the case of a continuous process, at least some of the liquid phase leaving the reactor is advantageously recirculated, preferably using a loop reactor.

A typical method for the epoxidation of olefins (especially of propylene into propylene oxide) in the presence of hydrogen peroxide and a heterogeneous catalyst is disclosed in the International patent application WO 99/48882 of SOLVAY SA, the content of which is enclosed herewith by reference. This patent application relates to a process for manufacturing 1,2-epoxypropane by reaction between propylene and a peroxide compound in the presence of a zeolite-based catalyst and a solvent, in which the pH of the reaction medium comprising propylene, the peroxide compound, the catalyst, the 1,2-epoxypropane formed and the solvent is from 4.8 to 6.5.

Another typical method for the epoxidation of olefins in the presence of hydrogen peroxide and a heterogeneous catalyst is disclosed in the International patent application WO 99/48883 of SOLVAY SA, the content of which is enclosed herewith by reference. This patent application relates to a continuous process for manufacturing an epoxide, according to which an olefin is reacted, in a reactor in the liquid phase, with a peroxide compound in the presence of a zeolite-based catalyst and in the presence of a solvent, and a gaseous compound is introduced continuously into the reactor at a flow rate which is sufficient to entrain at least some of the epoxide produced, which is recovered with the gaseous compound at the point at which it leaves the reactor. In a preferred embodiment of such process, the reactor is a loop-type reactor, for example a bubble-siphon loop-type reactor.

Another typical method for the epoxidation of olefins in the presence of hydrogen peroxide and a heterogeneous catalyst is disclosed in the European patent application EP 1122249 of SOLVAY SA, the content of which is enclosed herewith by reference. This patent application discloses a process comprising reacting an olefin and hydrogen peroxide in the presence of a catalyst and an organic diluent to form an oxirane, wherein the hydrogen peroxide is an aqueous hydrogen peroxide solution obtained by extraction, with substantially pure water, of a mixture derived from the oxidation of at least one alkyanthrahydroquinone, without a subsequent washing, purification treatment or combination thereof.

Another typical method for the epoxidation of olefins in the presence of hydrogen peroxide and a heterogeneous catalyst is disclosed in the International patent application WO 02/00634 of SOLVAY SA, the content of which is enclosed herewith by reference. This patent application relates to a continuous process for manufacturing an oxirane by reacting an olefin with a peroxide compound in the presence of a catalyst, a solvent and water in a plant comprising at least one reactor containing the catalyst and at least two distillation columns, according to which:
  the olefin, the solvent, the peroxide compound and the water are introduced into the reactor,
  an epoxidation of the olefin is carried out to form the oxirane,
  a medium comprising the oxirane formed, the unconverted olefin, the solvent, the unconsumed peroxide compound, the water and possibly by-products is removed from the reactor,
  the medium is introduced into a distillation column (A),
  a mixture containing the majority of the oxirane formed and unconverted olefin, solvent, water and possibly by-products is collected at the top of column (A),
  the mixture is introduced into a condenser to eliminate some of the unconverted olefin,
  the mixture depleted in unconverted olefin is collected in liquid form,
  the liquid mixture is introduced into a second distillation column (B),
  a mixture of solvent and water is collected at the bottom of column (B) and is recycled into the reactor, and
  an oxirane-based medium is collected at the top of column (B).

A further typical method for the epoxidation of olefins in the presence of hydrogen peroxide and a heterogeneous catalyst is disclosed in the International patent application WO 02/00635 of SOLVAY SA, the content of which is enclosed herewith by reference. This patent application discloses a process for manufacturing oxirane by reacting an olefin with a peroxide compound in the presence of a catalyst and a solvent in at least two reactors arranged in series, each of which contains a portion of the catalyst, according to which:
  a first portion of the olefin, the solvent and the peroxide compound are introduced into a first reactor, an epoxidation of the first portion of the olefin is carried out therein in order to form a first portion of the oxirane, a medium comprising the first portion of oxirane formed, the solvent, the unconverted olefin and, where appropriate, the unconsumed peroxide compound is removed from this reactor, the medium is introduced into a distillation column, the majority of the oxirane formed and of the unconverted olefin is collected at the top of the column, the medium depleted in oxirane and containing, where appropriate, the unconsumed peroxide compound is collected at the bottom of the column, the medium depleted in oxirane and another portion of the olefin and optionally another portion of the peroxide compound are introduced into a subsequent reactor, an epoxidation of the other portion of the olefin is carried out therein in order to form another portion of the oxirane, and the other portion of the oxirane thus formed is collected.

Another useful method for the epoxidation of olefins in the presence of hydrogen peroxide and a heterogeneous catalyst is disclosed in the International patent application WO 02/092586 of SOLVAY SA, the content of which is enclosed herewith by reference. In this process, the epoxidation reaction is conducted in a reactor containing a liquid phase, in the presence of water, one or more organic solvents, a catalyst and one or more compounds for increasing the selectivity of the catalyst towards epoxidation reactions, chosen from mineral or organic bases, mixtures of a salt and of its conjugate acid or base, salts, and mixtures thereof, in which:

if the process is performed in batchwise mode, the liquid phase present in the reactor when the reaction starts if the process is performed continuously, all of the liquid phases that are fed continuously into the reactor has/have a total organic solvent content of at least 0.1 g/kg and of not more than 675 g/kg.

The hydrogen peroxide solution of the present invention is especially useful for the manufacture of propylene oxide (or 1,2-epoxypropane) by reaction between propylene and hydrogen peroxide. It can also be used for the manufacture of epichlorohydrin by reaction between allyl chloride and hydrogen peroxide. It has indeed surprisingly been found that the apparent pH of the hydrogen peroxide solution has an impact on the selectivity when this solution is used for the epoxidation of these olefins (especially propylene into propylene oxide). It has further been found that the apparent pH of the solution depends on the hydrogen peroxide concentration [$H_2O_2$] expressed as % by weight of the solution. The use of a hydrogen peroxide solution having a pH lower than the optimal pH range leads to a lower selectivity. The use of a hydrogen peroxide solution having a pH higher than the optimal pH range leads to a lower selectivity and a lower conversion rate of the hydrogen peroxide. The use of a hydrogen peroxide solution having an optimal pH according to the present invention therefore leads to an optimal selectivity. In addition, the fact of using a hydrogen peroxide solution having such an optimal apparent pH does not impair the hydrogen peroxide conversion rate and can even improve it.

The present invention also relates to a process for the manufacture of propylene oxide by reaction between propylene and hydrogen peroxide, wherein an aqueous hydrogen peroxide solution according to the invention is used.

The present invention is further illustrated below without limiting the scope thereto.

EXAMPLES pH Measurements

The pH measurements were done according to a method based on the CEFIC PEROXYGENS $H_2O_2$ AM-7160 standard (March 2003).

Before taking the pH readings, the solutions were thermostatised at 20.0° C.±0.1° C. using a measurement cell with a double envelope and a recirculating water bath. The measurement cell is composed of borosilicate glass, has a volume of 150 mL and is fitted with a multi-necked cover (for the insertion of the electrode, the temperature probe and the nitrogen flow).

The pH meter was a model 827 from METROHM. The combined glass electrode which was used is an Aquatrode Plus from METROHM (6.02057.000), particularly suited for fast pH measurements in poorly conducting solutions. The electrode is equipped with a Pt 1000 temperature sensor and has a fixed ground-joint diaphragm, avoiding contamination of the reference compartment. The glass electrode was calibrated with respectively 75 mL of the two following buffer solutions:

buffer at pH 1.68 (20° C.), containing potassium tetraoxalate buffer at pH 4.00 (20° C.), containing potassium hydrogen phthalate.

75 mL of the sample were then placed in the clean, dry measuring cell. The cover was replaced and the air space was flushed with nitrogen (free from carbon dioxide). The electrode was immersed in the sample solution which was then agitated. The apparent pH of the sample was read directly from the meter when the reading stabilizes. The resolution of the pH meter is 0.01 pH unit, with temperature compensation and with slope control.

Examples 1 to 5

Comparison with a pH Lower than $pH_{min}$

For examples 1 and 2, an installation according to FIG. 1 has been used: A liquid flow called the "shuttle" was introduced via a pipe (2) into the bottom of a reactor (1) containing TS-1 in the form of beads consisting of 35% titanium silicalite dispersed in a silica matrix (65% by weight) and obtained by a process of sol-gel type. This flow comprised propylene, hydrogen peroxide, water, propylene oxide and its byproducts and methanol. The liquid flow circulated in the reactor in the direction of the arrows. On leaving the reactor, the reaction medium was depressurized by means of a valve (3). This depressurization was followed by the sparging of a gaseous compound using a flow meter (4) in a stripping column (5). A gas mainly consisting of the produced propylene oxide, unconverted propylene, nitrogen used for the stripping and traces of methanol, left the stripping column (5) via the pipe (6). The liquid phase leaving the top of the column was partly recycled into the reactor via the pipe (7) and partly removed via the overflow pipe (8). The $H_2O_2$ solution was added to the recycled fraction via the pipe (9), and methanol was added via the pipe (10). The mixture thus obtained then passed into a saturator (12) via a pump (11). This saturator was fed with propylene under pressure via a flow meter (13), and at its outlet were collected, on the one hand, a gaseous phase of undissolved propylene that left through the pipe (14) via a depressurization valve (15), and on the other hand, the shuttle that was fed into the reactor (1) via the pipe (2).

The methanol flow rate and the flow rate of nitrogen used for the stripping were adjusted to maintain a constant residence time in the plant. The flow rate of the overflow liquid was about 106-120 g/h. The shuttle circulation speed was 5 l/h.

The $H_2O_2$ degree of conversion and the PO/$C_3$f selectivity were estimated as follows:

(1) Calculation of the Degree of Conversion

The degree of conversion of the $H_2O_2$ was calculated from the $H_2O_2$ inlet and outlet flow rates.

$TC(\%) = 100 \times (H_2O_2$ used in mol/h — unconverted $H_2O_2$ in mol/h)/$H_2O_2$ used in mol/h with unconverted $H_2O_2 = H_2O_2$ conc. of the overflow liquid in mol/kg×overflow liquid flow rate in kg/h.

(2) Calculation of the $PO/C_3f$ Selectivity $PO/C_3f$ sel. (%) = $100 \times PO_{formed}/\Sigma(PO+\text{by-products})_{formed}$ The conditions of examples 1 and 2 are given in the Table 1.

TABLE 1

|  | Example 1 (comparative) | Example 2 (according to inv.) |
|---|---|---|
| TS-1 used (g) | 1.58 | 1.58 |
| T° reactor (° C.) | 67 | 55 |
| Conc. of fed $H_2O_2$ solution (% by weight) | 39 | 39 |

TABLE 1-continued

|  | Example 1 (comparative) | Example 2 (according to inv.) |
|---|---|---|
| pH of fed $H_2O_2$ solution | 1.68 | 1.99 |
| Flow rate of $H_2O_2$ solution (g/h) | 15.5 | 15.2 |
| $H_2O_2$ feed rate (mol/h) | 0.178 | 0.174 |
| $CH_3OH$ feed rate (ml/h) | 275 | 251 |
| Pe feed rate at the saturator (LN/h) | 86 | 95 |
| Saturator T° (° C.) | 77 | 71 |
| Saturator pressure (bar) | 8 | 6.5 |
| Pe conc. at the reactor inlet (mol/kg) | 1.36 | 1.57 |
| Plant residence time (h) | 4 | 4 |
| Residence time on catalyst (min) | 5.5 | 5.5 |

As examples 1 and 2 were conducted at two different temperatures, respectively 67 and 55° C., a further example (example 5) was calculated on the basis of example 2 and of the results of examples 3 and 4.

Examples 3 and 4 have been performed in a bubble siphon reactor as disclosed in patent application WO 99/48883, by reaction between propylene and hydrogen peroxide in the presence of methanol and of catalyst TS-1 used in the form of beads 0.5 mm in diameter.

They have been carried out at 55 and 68° C. and at 1.33 bar, with a continuous feed of hydrogen peroxide at a flow rate of 0.57 mol/h, using a 39 wt % $H_2O_2$ solution. The propylene flow rate was 250 lN/h. The initial $H_2O_2$ conversion in the zero-conversion loop was 2.0-2.5 mol/kg. The amount of catalyst used was 15 g of beads containing 5.25 g of TS-1.

The results obtained for examples 3 and 4 after a running time of 6 h are given in Table 2.

TABLE 2

| Example No. | Epoxidation temperature | $PO/C_3f$ Selectivity (2) after 6 hours (%) | Degree of conversion of $H_2O_2$ (1) (%) |
|---|---|---|---|
| 3 | 55 | 78 | 81 |
| 4 | 68 | 74 | 84.8 |

The results obtained for examples 1 and 2 after a running time of 24 h, as well as the result calculated for example 5, are summarized in Table 3.

TABLE 3

| Example No. | $[H_2O_2]$ (weight %) | Apparent pH | Epoxidation temperature | $PO/C_3f$ selectivity (2) after 24 hours (%) | Degree of conversion of $H_2O_2$ (1) (%) |
|---|---|---|---|---|---|
| 1 (comparative) | 39 | 1.68 | 67 | 85.5 | 96.6 |
| 2 (according to the invention) | 39 | 1.99 | 55 | 91.6 | 90.3 |
| 5 (calculated, according to the invention) | 39 | 1.99 | 68 | 87.6 | 94 |

For an aqueous hydrogen peroxide solution having a hydrogen peroxide concentration $[H_2O_2]$ of 39%, the optimal apparent pH of the hydrogen peroxide solution should be of from 1.99 to 2.19.

Example 5 is conducted according to the invention and leads to a selectivity of 87.6% after 24 hours. Comparative example 1 (apparent pH lower than $pH_{min}$ defined according to the present invention) shows a lower selectivity after 24 hours, namely 85.5%.

Examples 6 to 10

Comparison with a pH Higher than $pH_{max}$

The four tests of examples 6 to 9 have been carried out using the same installation as the one used for examples 1 and 2. The conditions of examples 6 to 9 are given in the Table 4.

Since Pe (propylene) is less soluble in a medium with a low methanol content, the pressure and temperature in the saturator were adjusted to keep the Pe concentration more or less constant.

TABLE 4

|  | Example 6 (comp.) | Example 7 (acc. to inv.) | Example 8 | Example 9 |
|---|---|---|---|---|
| TS-1 used (g) | 1.58 | 1.58 | 1.58 | 1.58 |
| T° reactor (° C.) | 56 | 55 | 55 | 55 |
| Conc. of the fed $H_2O_2$ solution (% by weight) | 9.8 | 39 | 9.8 | 38.7 |
| pH of fed $H_2O_2$ solution | 5.26 | 1.99 | — | — |

TABLE 4-continued

|  | Example 6 (comp.) | Example 7 (acc. to inv.) | Example 8 | Example 9 |
|---|---|---|---|---|
| Flow rate of $H_2O_2$ solution (g/h) | 60.9 | 15.2 | 59.8 | 15.1 |
| $H_2O_2$ feed rate (mol/h) | 0.172 | 0.174 | 0.169 | 0.173 |
| $CH_3OH$ feed rate (ml/h) | 130 | 251 | 130 | 230 |
| Pe feed rate at the saturator (l/h) | 49 | 47 | 21 | 16 |
| Saturator T° (° C.) | 26 | 64 | 58 | 65 |
| Saturator pressure (bar) | 9.2 | 4.5 | 8 | 2.6 |
| Pe concentration at the reactor inlet (mol/kg) | 0.47 | 0.69 | 0.22 | 0.27 |
| Plant residence time (h) | 4 | 4 | 4 | 4 |
| Residence time on catalyst (min) | 5.5 | 5.5 | 5.5 | 5.5 |

The 10 wt % $H_2O_2$ solution used in the example 6 has been prepared by dilution from a 39 wt % solution having an apparent pH equal to 3.80.

As examples 6 and 7 were conducted at two different methanol feed rates, respectively 130 and 251 ml/h, a further example (example 10) was calculated on the basis of example 7 and of the results obtained for examples 8 and 9, for which the pH was not measured.

The results obtained for examples 8 and 9 after a running time of 24 h are given in Table 5.

TABLE 5

| Example No. | $CH_3OH$ feed rate (ml/h) | $PO/C_3f$ Selectivity (2) after 24 hours (%) | Degree of conversion of $H_2O_2$ (1) (%) |
|---|---|---|---|
| 8 | 130 | 79.4 | 84.7 |
| 9 | 230 | 83.9 | 76.4 |

The results obtained for examples 6 and 7 after a running time of 24 h, as well as the result calculated for example 10, are summarized in table 6 below.

TABLE 6

| Example No. | $[H_2O_2]$ (weight %) | Apparent pH | MeOH Flow rate (ml/h) | $PO/C_3f$ Selectivity (2) after 24 hours (%) | Degree of conversion of $H_2O_2$ (1) (%) |
|---|---|---|---|---|---|
| 6 (comparative) | 9.8 | 5.26 | 130 | 82.7 | 70.7 |
| 7 (according to the invention) | 39 | 1.99 | 250 | 89.9 | 86.2 |
| 10 (calculated, according to the invention) | 39 | 1.99 | 130 | 85.4 | 94.5 |

For an aqueous hydrogen peroxide solution having a hydrogen peroxide concentration $[H_2O_2]$ of 39%, the optimal apparent pH of the hydrogen peroxide solution should be of from 1.99 to 2.19. For a hydrogen peroxide concentration $[H_2O_2]$ of 9.8%, the optimal apparent pH of the hydrogen peroxide solution should be between 3.09 and 3.29.

The results of Table 6 show that, when the pH is above $pH_{max}$, a selectivity decrease is observed after 24 hours (from 85.4 to 82.7%) as well as a considerable decrease in the degree of conversion of $H_2O_2$ (from 94.5 to 70.7%).

The invention claimed is:

1. A process for the manufacture of propylene oxide or epichlorohydrine, the process comprising reacting propylene or allyl chloride and hydrogen peroxide, wherein the hydrogen peroxide comprises an aqueous solution having a hydrogen peroxide concentration $[H_2O_2]$ expressed as % by weight of the solution and an apparent pH less than 2.60, and wherein the apparent pH is also greater than or equal to $pH_{min}$ and less than or equal to $pH_{max}$, wherein $pH_{min}$ and $pH_{max}$ are defined by the following equations:

$$pH_{min}=3.45-0.0377\times[H_2O_2], \text{ and } pH_{min}<2.60; \text{ and}$$

$$pH_{max}=3.76-0.0379\times[H_2O_2], \text{ and } pH_{max}<2.60.$$

2. The process according to claim 1, wherein the aqueous hydrogen peroxide solution comprises a TOC content of from 0.01 to 500 ppm based on the weight of the solution.

3. The process according to claim 2, wherein the TOC contains at least one organic compound selected from the group consisting of dimethylheptanol, diisobutylcarbinol, 2,6-dimethyl-1,4-heptanediol, methyl cyclohexyl acetate, methyl cyclo hexanol, tetrabutyl urea, trioctylophosphate, and degradation products of alkylated aromatic solvents.

4. The process according to claim 1, wherein the aqueous hydrogen peroxide solution comprises a TOC content of from 100 to 500 ppm based on the weight of the solution.

5. The process according to claim 1, wherein the aqueous hydrogen peroxide solution comprises an acid concentration measured by titration of from 0.1 to 5 mmol/l.

6. The process according to claim 1 further comprising adjusting the apparent pH of the aqueous hydrogen peroxide solution by adding a strong mineral acid, (preferably nitric acid and/or phosphoric acid).

7. The process according to claim 1, wherein the aqueous hydrogen peroxide solution comprises alkaline and alkaline earth metals in an amount of from 1 to 200 ppm based on the weight of the solution.

8. The process according to claim 1, wherein the aqueous hydrogen peroxide solution comprises at least one stabilizer selected from the group consisting of nitric acid, phosphoric acid, benzoic acid, dipicolinic acid (DPA), nitrate, phosphate, pyrophosphate, stannate, benzoate, salicylate, diethylene triamine penta (methylene phosphonate), and mixtures thereof.

9. The process according to claim 1, wherein the aqueous hydrogen peroxide solution comprises at least one stabilizer selected from the group consisting of nitric acid, phosphoric acid, di-sodium pyrophosphate, ammonium nitrate, sodium nitrate, sodium stannate, and mixtures thereof.

10. The process according to claim 1, wherein the aqueous hydrogen peroxide solution comprises anions in an amount of from 50 to 200 ppm based on the weight of the solution.

11. The process according to claim 1, wherein the aqueous hydrogen peroxide solution comprises a hydrogen peroxide concentration of from 32 to 50% by weight.

12. The process according to claim 1, wherein the aqueous hydrogen peroxide solution comprises a hydrogen peroxide concentration of from 38 to 42% by weight.

13. The process according to claim 1, wherein the aqueous hydrogen peroxide solution comprises a hydrogen peroxide concentration of from 38 to 42% by weight, an apparent pH comprised in the range of from $pH_{min}$ to $pH_{max}$ defined respectively of from 2.02 to 1.87 and of from 2.31 to 2.17, a TOC content of from 150 to 220 ppm, a content of alkaline and alkaline earth metals of from 20 to 30 ppm, and an anion content of from 100 to 300 ppm.

14. The process according to claim 1, further comprising preparing the aqueous hydrogen peroxide solution according to an anthraquinone loop process comprising:
   a) hydrogenating a working solution comprising at least one organic solvent and at least one anthraquinone compound;
   b) oxidating the hydrogenated working solution to form hydrogen peroxide;
   c) extracting the hydrogen peroxide with an aqueous medium;
   d) optionally adding a stabilizer to the extracted aqueous hydrogen peroxide solution;
   e) concentrating or diluting the aqueous hydrogen peroxide solution to the desired hydrogen peroxide concentration; and
   f) optionally adapting the pH of the aqueous hydrogen peroxide solution by adding thereto a sufficient amount of an acid or a base.

15. A process for the epoxidation of olefins, the process comprising reacting hydrogen peroxide with an olefin in the presence of a heterogeneous catalyst, wherein the hydrogen peroxide comprises an aqueous solution having a hydrogen peroxide concentration [$H_2O_2$] expressed as % by weight of the solution and an apparent pH less than 2.60, and wherein the apparent pH is also greater than or equal to $pH_{min}$ and less than or equal to $pH_{max}$, wherein $pH_{min}$ and $pH_{max}$ are defined by the following equations:

$$pH_{min}=3.45-0.0377\times[H_2O_2], \text{ and } pH_{min}<2.60; \text{ and}$$

$$pH_{max}=3.76-0.0379\times[H_2O_2], \text{ and } pH_{max}<2.60.$$

16. The process according to claim 15, wherein the aqueous hydrogen peroxide solution comprises a TOC content of from 0.01 to 500 ppm based on the weight of the solution.

17. The process according to claim 16, wherein the TOC contains at least one organic compound selected from the group consisting of dimethylheptanol, diisobutylcarbinol, 2,6-dimethyl-1,4-heptanediol, methyl cyclohexyl acetate, methyl cyclo hexanol, tetrabutyl urea, trioctylophosphate, and degradation products of alkylated aromatic solvents.

18. The process according to claim 15, wherein the aqueous hydrogen peroxide solution comprises a TOC content of from 100 to 500 ppm based on the weight of the solution.

19. The process according to claim 15, wherein the aqueous hydrogen peroxide solution comprises an acid concentration measured by titration of from 0.1 to 5 mmol/l.

20. The process according to claim 15 further comprising adjusting the apparent pH of the aqueous hydrogen peroxide solution by adding a strong mineral acid, (preferably nitric acid and/or phosphoric acid).

21. The process according to claim 15, wherein the aqueous hydrogen peroxide solution comprises alkaline and alkaline earth metals in an amount of from 1 to 200 ppm based on the weight of the solution.

22. The process according to claim 15, wherein the aqueous hydrogen peroxide solution comprises at least one stabilizer selected from the group consisting of nitric acid, phosphoric acid, benzoic acid, dipicolinic acid (DPA), nitrate, phosphate, pyrophosphate, stannate, benzoate, salicylate, diethylene triamine penta (methylene phosphonate), and mixtures thereof.

23. The process according to claim 15, wherein the aqueous hydrogen peroxide solution comprises at least one stabilizer selected from the group consisting of nitric acid, phosphoric acid, di-sodium pyrophosphate, ammonium nitrate, sodium nitrate, sodium stannate, and mixtures thereof.

24. The process according to claim 15, wherein the aqueous hydrogen peroxide solution comprises anions in an amount of from 50 to 200 ppm based on the weight of the solution.

25. The process according to claim 15, wherein the aqueous hydrogen peroxide solution comprises a hydrogen peroxide concentration of from 32 to 50% by weight.

26. The process according to claim 15, wherein the aqueous hydrogen peroxide solution comprises a hydrogen peroxide concentration of from 38 to 42% by weight.

27. The process according to claim 15, wherein the aqueous hydrogen peroxide solution comprises a hydrogen peroxide concentration of from 38 to 42% by weight, an apparent pH comprised in the range of from $pH_{min}$ to $pH_{max}$ defined respectively of from 2.02 to 1.87 and of from 2.31 to 2.17, a TOC content of from 150 to 220 ppm, a content of alkaline and alkaline earth metals of from 20 to 30 ppm, and an anion content of from 100 to 300 ppm.

28. The process according to claim 15, further comprising preparing the aqueous hydrogen peroxide solution according to an anthraquinone loop process comprising:
   a) hydrogenating a working solution comprising at least one organic solvent and at least one anthraquinone compound;
   b) oxidating the hydrogenated working solution to form hydrogen peroxide;
   c) extracting the hydrogen peroxide with an aqueous medium;
   d) optionally adding a stabilizer to the extracted aqueous hydrogen peroxide solution;
   e) concentrating or diluting the aqueous hydrogen peroxide solution to the desired hydrogen peroxide concentration; and
   f) optionally adapting the pH of the aqueous hydrogen peroxide solution by adding thereto a sufficient amount of an acid or a base.

* * * * *